(12) United States Patent
Vessey et al.

(10) Patent No.: US 7,998,742 B2
(45) Date of Patent: Aug. 16, 2011

(54) FLUORESCENT ASSAY

(75) Inventors: John Phillip Vessey, East Horsley (GB); Adrian Richard Gray, Workingham (GB)

(73) Assignee: Quotient Diagnostics Limited, Walton on Thames, Surrey (GB)

( * ) Notice: Subject to any disclaimer, the term of this patent is extended or adjusted under 35 U.S.C. 154(b) by 197 days.

(21) Appl. No.: 12/295,575

(22) PCT Filed: Mar. 23, 2007

(86) PCT No.: PCT/GB2007/050147
§ 371 (c)(1),
(2), (4) Date: Sep. 30, 2008

(87) PCT Pub. No.: WO2007/113590
PCT Pub. Date: Oct. 11, 2007

(65) Prior Publication Data
US 2009/0176309 A1     Jul. 9, 2009

(30) Foreign Application Priority Data

Mar. 31, 2006   (GB) .................................. 0606450.5

(51) Int. Cl.
*G01N 33/72* (2006.01)
*G01N 21/76* (2006.01)

(52) U.S. Cl. .............. 436/67; 436/63; 436/66; 436/164; 436/172; 422/52; 422/82.05; 422/82.08

(58) Field of Classification Search ................... 436/63, 436/66, 67, 164, 172; 422/68.1, 73, 82.05, 422/82.08, 52
See application file for complete search history.

(56) References Cited

U.S. PATENT DOCUMENTS

| | | | | |
|---|---|---|---|---|
| 4,861,728 A | * | 8/1989 | Wagner | 436/501 |
| 5,242,842 A | * | 9/1993 | Sundrehagen | 436/536 |
| 5,478,754 A | * | 12/1995 | Brandt et al. | 436/518 |
| 5,877,025 A | * | 3/1999 | Edwards et al. | 436/67 |

OTHER PUBLICATIONS

Mertens et al. Analytical Biochemistry, vol. 96, issue 2, Jul. 15, 1979, pp. 448-455.*
Blincko et al. (abstract) Annals of Clinical Biochemistry, vol. 37, No. 3, pp. 372-379, 2000.*

* cited by examiner

*Primary Examiner* — Maureen M Wallenhorst
(74) *Attorney, Agent, or Firm* — Fox Rothschild LLP

(57) ABSTRACT

A method and apparatus to estimate the concentration of a non-fluorescent substance (e.g. haemoglobin) in a fluorescent assay by separately estimating the non time dependent alteration attributed to inherent filter effects from the time dependent alteration caused by the assay chemistry. Such a method obviates the requirement for a separate photometric or other measurement thereby simplifying the methodology and associated instrumentation.

19 Claims, 5 Drawing Sheets

FLUORESCENT ASSAY

The present invention relates to methods of carrying out an assay for a non-fluorescent substance in a sample, and further relates to apparatus for conducting assays according to such methods.

European patent number EP 0,772,779 describes the assay of glycated proteins by fluorescence quenching. The prior art as exemplified by this document describes the assay of glycated haemoglobin using the quenching of fluorescence produced when said glycated haemoglobin binds to a conjugate produced by the chemical linking of specific fluorophors to boronic acid groups. This concentration dependent quenching is then compared to a measure of total haemoglobin made by conventional photometric means, which is established prior art.

However during this prior art method there is an unavoidable non-specific level of fluorescence quenching that is not caused by the binding of said conjugate to glycated haemoglobin but instead by an inherent filter effect. This inherent filter effect is caused by the haemoglobin molecule per se absorbing both the exciting radiation and the emitted fluorescent light caused by the spectral overlap of the haemoglobin absorption spectrum with the fluorescence excitation and emission spectra. This background fluorescence quenching must be compensated for in calculation in order to allow quantification of the specific quenching that is attributed solely to the concentration of glycated haemoglobin and hence its quantum. The inventors of EP 0,772,779 achieved this by determining the optical density of the reaction solution at a suitable wavelength (e.g. 405 nm or 415 nm) and subtracting a pro rata element of the total fluorescence quenching dependent on this optical density measurement.

In the method disclosed in EP 0,772,779 the total haemoglobin concentration is measured using conventional photometric methods such as absorbance at 405 nm or 415 nm. For that method to function as described therein the user must make two independent measurements on separate instruments: a photometer to measure the total optical density and a fluorimeter to measure the fluorescence quenching. For the test to have any commercial utility, for example in the management of diabetes, any instrument designed and manufactured specifically for the test must consequently have the dual functionality of both a fluorimeter and a photometer. This is costly, more complex and undesirable.

The quenching of fluorescence by haemoglobin as described in EP 0,772,779 has two constituents. The first, an initial instantaneous drop in fluorescence associated with the haemoglobin specimen acting like a neutral density filter at the fluorescence excitation and emission wavelengths; and the second a time dependent quenching of the fluorescence signal associated with the time course of the chemical binding of glycated haemoglobin to the fluorescent conjugate reagent.

The present invention aims to overcome the problems of the prior art method, as described above and further discussed below, in the hope of developing a significantly improved assay method, as well as to design instruments automatically to achieve the desired results. As a result of this careful study, the present inventors have ascertained that by following the fluorescence alteration time course as the assay reaction progresses, the background fluorescence alteration, i.e. an instantaneous decrease or increase not dependent upon the reaction chemistry, can be determined separately from the time dependent fluorescence quenching attributed to the chemical binding of the target compound to the fluorescent reagent. Leading on from this they have also found that an alteration in detected fluorescence, in particular a quenching effect, when a substance is added to a fluorescent reagent can be used to calculate the concentration of that substance which is not itself fluorescent.

According to a first aspect of the present invention there is provided a method of carrying out an assay for a non-fluorescent substance in a sample, which method comprises:

(a) carrying out a reaction in solution between an assay sample and a fluorescent marker compound, the sample and marker compound being combined at time $t_0$;

(b) exciting the fluorescence in the marker compound, wherein the nature of the marker and the nature of the excitation are such that the said fluorescence occurs at a wavelength at which said fluorescence is altered by the reaction of the marker compound with the non-fluorescent substance;

(c) detecting the resulting fluorescence as the reaction progresses;

(d) calculating from the detected fluorescence the values of $F_0$ being the fluorescence at time $t_0$ and $F_\infty$ being the fluorescence at time $t_\infty$, which is the point at which all of the non-fluorescent substance has reacted with the marker compound, or the reaction has attained equilibrium;

(e) calculating from the values of $F_0$ and $F_\infty$ the background change in fluorescence attributable to the reaction in step (a); and (f) determining from the calculated values and a suitable calibration algorithm the concentration of the non-fluorescent substance present in the sample at $t_0$ prior to reacting with the fluorescent marker compound.

As used herein, when referring to the substance to be assayed (the analyte) the term non-fluorescent does not mean that the substance is totally non-fluorescent. Instead it means that is has a different excitation and or emission spectra to the fluorescent marker compound at the relevant excitation and emission wavelengths.

A major currently intended use of the present invention is in the assaying of glycated haemoglobin in blood. Indeed, the genesis of the present invention lies in improving a process for this assay, and in particular assaying the amount or proportion of glycated haemoglobin (i.e. haemoglobin to which glucose has become non-enzymatically bound) within a sample. For this reason the following description will often describe the invention in respect of this, though the present invention is equally applicable to the assaying of many different substances—in particular such substances where the absorption characteristics of the contents of the sample are prone to interfere with the fluorescent characteristics of an appropriate fluorophor.

The first aspect of the present invention requires a marker compound that is specific for the substance to be assayed and the fluorescence of which is appropriately altered (possibly increased, but more usually decreased) by the binding of the marker to the substance.

The marker compound will usually comprise a fluorophor and a linking group adapted to bind selectively to the substance. The selection of an appropriate fluorophor and linking group combination for a particular target substance may be made based on experimental testing or on the known characteristics of existing fluorophors and linking groups relative to the substance to be assayed. A range of known fluorophors is mentioned in EP 772,779, the content of which is incorporated herein by reference. For a glycated protein such as glycated haemoglobin a suitable marker could include a boronic acid group bound by a connecting group to a fluorescein derivative. The boronic acid binds to the cis-diol group of a glycated protein but is not protein specific. It is preferred that the method is adapted specifically for the detection of glycated haemoglobin and a suitable marker for this might have the formula:

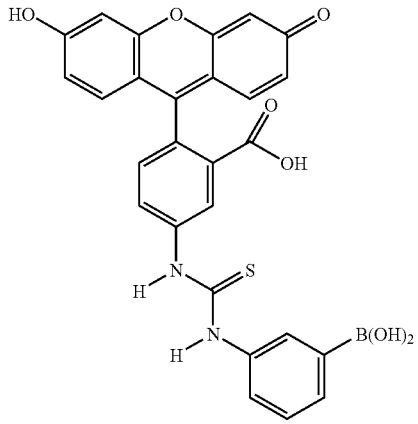

I

The calibration algorithm used in section (f) may be of the form y=mx+c, where m and c are the slope and intercept calibration constants and x=$(F_0-F_\infty)/F_0$. The target non-fluorescent substance may be a subspecies (e.g. glycated haemoglobin) of a main substance (e.g. total haemoglobin in all forms), and the subspecies will be selectively reactive with the marker compound as compared to the main substance. In such a case it may be desirable to known the overall concentration of the main substance (including the subspecies) present in the sample at $t_0$, prior to reacting with the fluorescent marker compound. This may be determined from the calculated values and a suitable calibration algorithm of the form y=m'x+c'; where m' and c' are the slope and intercept calibration constants and x=Log $(F_{Blank}/F_0)$.

The calculation of the values of $F_0$ and $F_\infty$ in step (d) preferably includes plotting the detected fluorescence data against time, and applying a best fit curve to the plotted points. The plotting may be physical or even manual, but is often achieved automatically and mathematically by fitting a mathematical function of a curve of best fit to the data and extrapolating that function to time $t_0$ and $t_\infty$, without the generation of a graph as such. The curve fitting may be achieved by any suitable mathematical method, and two particularly appropriate ones are described later in this specification. Using these regimes the recorded data is used to minimise variance and then the curve is extrapolated to provide values for $F_0$ and $F_\infty$.

In a fully automated instrument system, where blood is added to the reagent and mixed by the instrument, the initial quenching might possibly be determined within the first 5 seconds or so after blood addition and mixing. However, in a non-automated system, the monitoring of the initial binding reaction is further delayed due to the finite time required by an operator physically to add the blood specimen to the reaction cuvette containing the reagent, mix and return the reaction cuvette to the fluorimeter. Therefore, the actual fluorescence level at to, immediately after the addition of the blood specimen, cannot directly be measured in either the manual or automatic system. To overcome this, the fluorescence level $F_0$ at time $t_0$ i.e. immediately after sample addition and mixing but before reaction has occurred, is determined by back extrapolation of a curve fitted to the time course fluorescence data, based upon the rate equation of the chemical binding reaction. Further, by forward extrapolation of this curve fit beyond the data collection period, the fluorescence level $F_\infty$ at time $t_\infty$, the reaction end-point, is also determined. Determining the fluorescence levels at $t_0$ and $t_\infty$ in this manner has been shown to produce reliable and accurate results.

The time period over which the fluorescence of the reaction mixture is measured may be anything suitable for the use to which the assay is put. A long period gives greater accuracy, but a slower assay process, whereas a short period is convenient, but may lead to less precise results as the amount of data from which to extrapolate becomes sparse. The suitable length of the measurement period will depend on the substance being assayed and the time profile of its reaction with the fluorescent marker. In respect of haemoglobin boronate binding to cis diol groups, a measurement period of about 3 minutes is usually appropriate.

It is preferred that before the sample is combined with the marker compound in step (a), the marker compound alone (which is usually in the form of a reagent solution) is excited by incident electromagnetic radiation of a suitable wavelength $\lambda_n$ (i.e. the same as that at which excitation occurs during reaction with the sample) and the resultant initial fluorescence ($F_{Blank}$) at the emission frequency is detected. This in combination with the value of $F_0$ can be used to calculate initial alteration in the fluorescence, which in turn may be used to calculate the fluorescence optical density (FOD) using the equation:

$$\text{FOD} = \text{Log}\,[F_{Blank}/F_0] \qquad \text{(Equation 1)}$$

This log function of the initial background alteration (usually a quenching effect) is designated as FOD. FOD has been found to be directly proportional to the optical density of the reaction solution at a given wavelength. In the instance where the assay concerns haemoglobin, it is proportional to the optical density measured at 415 nm (See FIG. 3). As the optical density, at 415 nm, is in turn proportional to total haemoglobin concentration, the measurement of background fluorescence quenching can therefore also be used to determine total haemoglobin concentration. This background fluorescence quenching determination of total haemoglobin can therefore be used to replace the optical density determination, otherwise made by a separate photometric apparatus.

It may not be necessary to determine $F_{Blank}$ before every assay, as this value may be a standard or constant value depending on the reaction cuvette and the marker compound reagent used.

According to a second aspect of the present invention there is also provided a method of determining the concentration of a non-fluorescent substance, comprising exciting a matching fluorescent reagent the excitation and emission spectrum of which overlaps the absorption spectrum of the non-fluorescent substance; detecting the resultant fluorescence; adding the non-fluorescent substance to the matching fluorescent reagent; detecting the fluorescence after the addition; and calculating the concentration of the non-fluorescent substance from the difference between the fluorescence detected before and after addition of the non-fluorescent substance.

It is well known to calculate the concentration of a substance in solution using optical density measurements in comparison to established standards. However the second aspect of the present invention allows a concentration to be experimentally derived without the use of a photometer.

The method of the second aspect of the invention can be used where there is no reaction between the non-fluorescent substance and the reagent, which may be similar to the marker compound described above. However there may be a time dependent reaction that alters (either to increase or decrease) the detected fluorescence. By monitoring this and plotting a graph (either actually or notionally) as described with respect to the first aspect, the value of the initial alteration effect may be accurately estimated by extrapolation from the measured data.

When measuring the concentration of a substance that does not react with the marker to change the fluorescence, there is no need to extrapolate as the fluorescence measurement taken some time after addition of the sample will be the same as that immediately thereafter. But when the sample and reagent react, the back extrapolation to $t_0$ may be used to overcome the inability to measure the $F_0$ value directly.

Since the various aspects of the present invention describe means for making accurate determination of the amount or concentration of a substance present or the amount of a sub-species of that substance (such as the level of glycated haemoglobin within the total haemoglobin) that is present from the analysis of the fluorescence data alone, the design and construction of any associated instrument is greatly simplified, with costs substantially reduced as a consequence. In particular, simpler apparatus not including a spectrophotometer may be used to give better results.

According to a third aspect of the present invention there is yet further provided apparatus for the assay of a substance in a sample and using a fluorescent marker compound, which apparatus comprises:

(a) a reaction vessel adapted to hold an amount of the fluorescent marker compound and an assay sample, which marker compound together with the substance in the sample undergo a reaction beginning at time $t_0$ and ending at time $t_\infty$ that alters the fluorescent characteristics of the marker compound;

(b) a source of electro-magnetic radiation having a wavelength $\lambda_n$ to excite the fluorescence in the marker compound;

(c) detecting means to measure the resulting fluorescence as the reaction progresses; and (d) a processor adapted: (1) to calculate from the measured fluorescence the values of $F_0$ being the fluorescence at time $t_0$ and $F_\infty$ being the fluorescence at time $t_\infty$, when all of the substance has reacted with the marker compound; (2) to calculate any background change in fluorescence not attributable to and that attributable to the reaction between the substance and the marker compound; and (3) to determine from the calculated values the amount of the non-fluorescent substance and/or a sub-species thereof present in the sample at $t_0$.

For the aspects of present invention to have a benefit, at least one constituent element of the sample—be it the substance that is to be quantified, a related substance that needs quantification in contrast to the desired substance, or a contaminant—must have an absorption spectrum that overlaps to some degree with the excitation and emission spectra of the fluorescent marker/reagent. Consequently the wavelength of the exciting radiation and the nature of the fluorescent marker must be matched to each other and selected based upon the nature of the assay to be performed, which in turn includes the characteristics of the substance to be quantified and other substances liable to be found in the sample.

Many modifications of the methods and apparatus of the present invention described herein will be apparent to the skilled man and these modifications fall within the scope of the present invention. However in order that its principles may be better understood, but by way of example only, the present invention will now be described in detail with reference to certain examples and where appropriate to the accompanying drawings in which.

Figure 1:
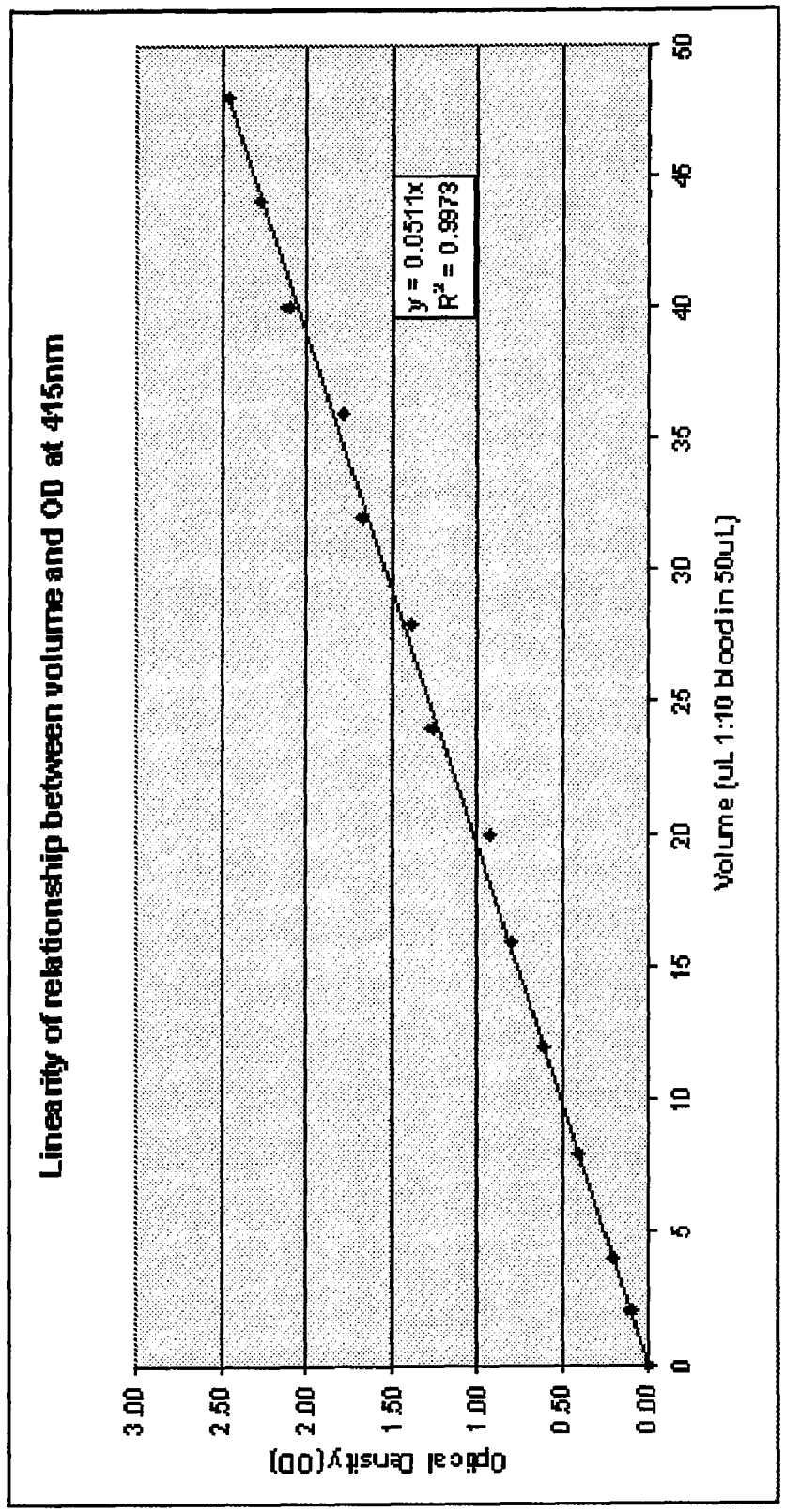
FIG. 1 is a graph depicting the relationship between optical density (OD) at 415 nm and quantity of haemoglobin added.
Figure 2:
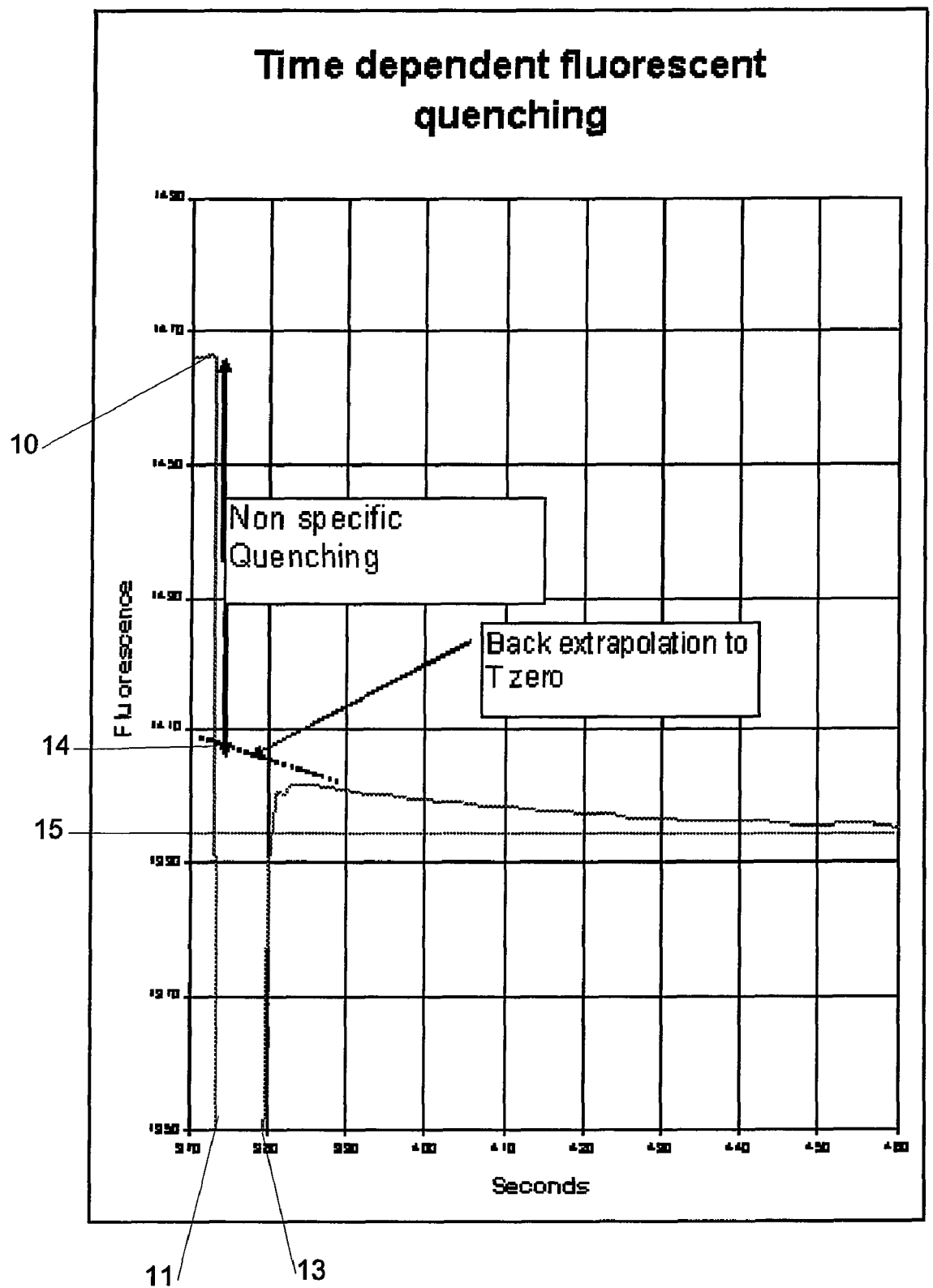
FIG. 2 is a plot of the fluorescence signal time course during a glycated haemoglobin/eosin-boronic acid binding reaction.

The present invention may be used to assay haemoglobin and in particular glycated haemoglobin in blood. In such a method the fluorescent marker compound, which may be fluorescein-boronic acid or as in this example an eosin-boronic acid compound, is introduced into a cuvette and prior to the introduction of a blood specimen, is excited in a fluorimeter by EM radiation at a suitable wavelength (510 nm) and the fluorescence blank ($F_{Blank}$) is measured by detecting emission at 580 nm. These wavelengths were chosen because with a move off the Eosin Y excitation peak improved assay performance is found. The chosen excitation wavelength corresponding to a point where the absorption spectra of the many different haemoglobin species found in blood (i.e. carboxy-haemoglobin, oxy-, deoxy-, met- etc.) has the smallest variation. Likewise the emission wavelength monitored, 580 nm (with a 40 nm bandpass), is chosen so as to minimise differences between the integrated absorption, over the emission bandpass, for the various haemoglobin species. The cuvette is removed from the fluorimeter or left in place and the blood sample is immediately added and mixed and the fluorescence over a time course is detected and recorded. This data is plotted and a curve is fitted to the data set. FIG. 2 shows such a reaction time profile where the initial fluorescence $F_{Blank}$ labelled 10 is recorded prior to sample introduction at $t_0$ (11). The actual experimental fluorescence data for the reaction is recorded over time (usually at 1 second intervals) from the reintroduction of the cuvette in a manual system or after mixing in an automatic system at point 13 until a suitable period has elapsed. By back extrapolation, the fluorescence level, $F_0$ (see point marked 14) is determined at $t_0$ (11), i.e. the point when the sample was added but no reaction with the marker had occurred. By forward extrapolation (which is not shown because the end of the measure data is off the graph in FIG. 2) the fluorescence level $F_\infty$ (15) at the reaction endpoint $t_\infty$ is similarly determined.

Two of many potential curve fit routines have been shown to be effective in the extrapolated estimation of $F_0$ and $F_\infty$ and the subsequent derivation of FOD and the specific quenching.

In the first an estimate $F_{t\text{-}estimate}$ is made based on the fluorescence measured $F_{t\text{-}actual}$ at each of the one second measurement points throughout the 3 minute assay, using a curve fitting routine based upon the general rate equation below (Equ. 2)

$$F_t = F_0 + (F_\infty - F_0) \times (1 - e^{-t/\theta}) \qquad \text{Equ. 2}$$

where, $F_t$=Fluorescence at time t seconds
$F_0$=Fluorescence at time zero
$F_\infty$=Fluorescence at time infinity (i.e. at reaction end)
e=2.7813 (natural log base)
θ=rate constant with $F_0$, $F_\infty$ and θ being determined iteratively by minimising the sum of the squared variances between the fitted and measured value at each one second data point, i.e. $\Sigma(F_{t\text{-}actual} - F_{t\text{-}estimated})^2$ is minimised by the fitting routine.

The second approach uses the rate equation for a second order chemical reaction in place of the general rate equation (Equ. 2) used above. Whereby:

$$A+B \rightarrow C$$

$$V_0 = k[A][B]$$

where,
$V_0$ is the rate of reaction,
k=rate constant
The rate constant, k, is defined by $$k = A \cdot e^{-E/(RT)}$$

where,
E=constant,
A=activation energy,
R=gas constant and
T=Absolute temperature $V_0$ is used to calculate the fluorescent intensity for each second, the concentrations of the reactants modified and $V_0$ then re-calculated for the next time point. An iterative procedure minimises the sum of the squared variances between the estimated value and the measured value by adjusting the values for E, A and R as in the previous example.

However, it should be noted that at least in respect of haemoglobin quantification the present invention relates to the principles of estimating the initial fluorescence drop caused by the quenching of fluorescence due to the inherent filter effect of haemoglobin, and then possibly using this to estimate the concentration of the substance or indeed any quenching material in the sample. The mathematical modelling of the data can be achieved by other methods of curve fitting which may be equally acceptable in practice.

The FOD parameter, fluorescence optical density, is determined via the following expression:

$$FOD = Log [F_{Blank}/F_0] \qquad \text{Equ. 1}$$

Figure 3:
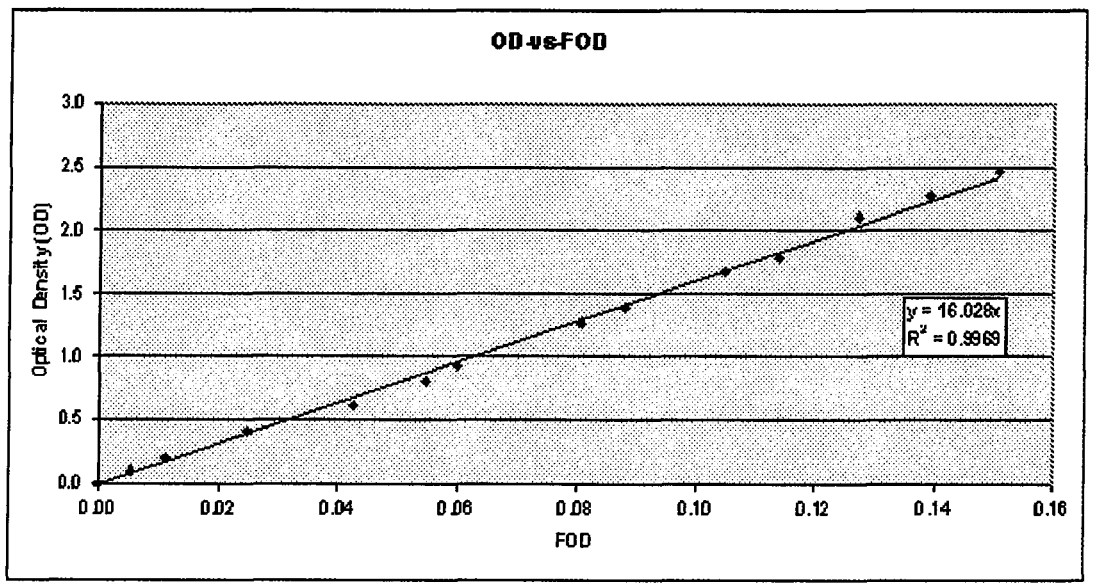
FIG. 3 is a graph showing the relationship between OD at 415 nm and FOD derived from the background fluorescence quenching.

FOD has been found to be linearly related to the total haemoglobin concentration. Haemoglobin concentration has been shown to be proportional to the optical density of a blood sample and 415 nm and FIG. 3 shows that FOD is directly proportional to the OD of the sample. The initial alteration, which when assaying blood samples for haemoglobin is a drop (or quenching), when calculated as a log function (FOD), is correlated to the measurement of haemoglobin by absorption photometry at other wavelengths.

Figure 4:
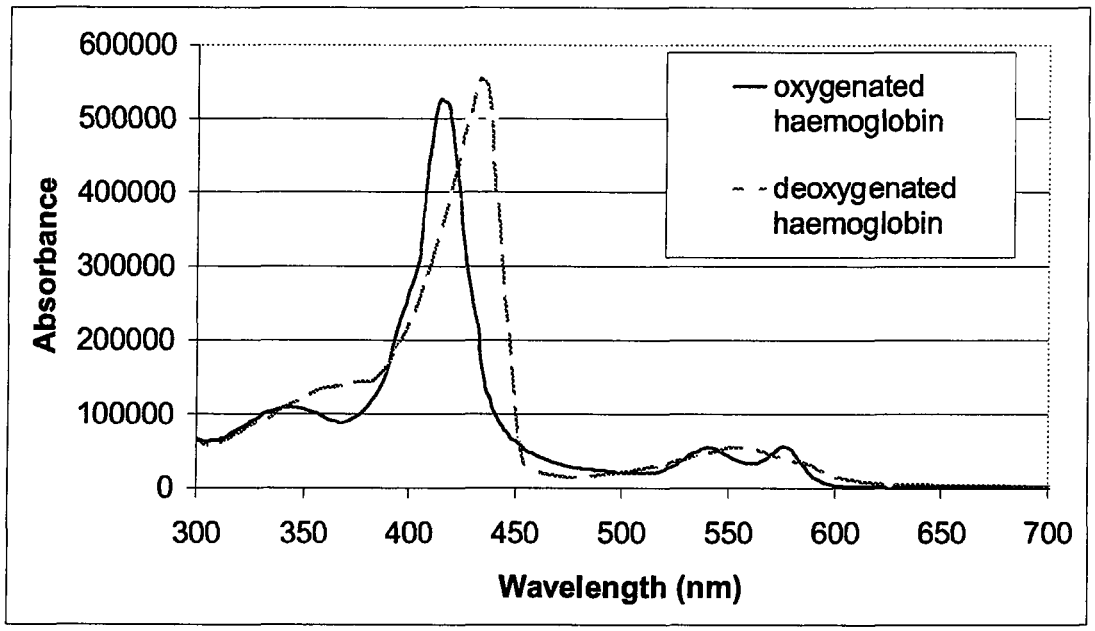
FIG. 4 is a graph showing the spectral differences between different haemoglobin types.

In addition to the benefits discussed above, the present invention also has other important beneficial consequences particularly in the assay of blood for the presence or quanta of glycated haemoglobin. Haemoglobin in red blood cells exists in a variety of states depending on the oxygenation status of the donor's blood and his/her physiological condition. Deoxyhaemoglobin, oxyhaemoglobin, carboxyhaemoglobin, sulphydryl haemoglobin and met-haemoglobin are some of the types, or chemical modifications of, haemoglobin that may be present in blood samples in varying amounts depending on their age and source. Each type of haemoglobin is characterised by a unique absorption spectrum when subjected to light of varying wavelengths (see FIG. 4 for a comparison of oxyhaemoglobin and deoxyhaemoglobin). Stored and processed blood samples in particular accumulate a significant proportion of met-haemoglobin, where the ferric ion is oxidised, changing its absorption spectrum and accounting for its deep red/brown colouration.

The prior art as exemplified by EP 0,772,779 does not appreciate or counter the influence of the state of the haemoglobin molecule with its associated absorption spectrum, on its ability to quench fluorescence both by virtue of its intrinsic absorption and also by virtue of its spectral overlap with the fluorescent conjugate. Instead it expects that a measurement of haemoglobin at either 405 or 415 nm accurately predicts the initial quenching drop caused by the presence of the haemoglobin in the sample. This is only true for haemoglobin samples that have identical spectra since the initial quenching drop is caused by secondary haemoglobin absorption peaks which correspond to the excitation and emission wavelengths $\lambda_n$ of the fluorophor used. It is the secondary absorption peaks that show most variability between haemoglobin states.

These differences in haemoglobin types in the assay are so significant that in order to calibrate the assay, standards having the same composition of haemoglobin types as the unknown samples under investigation must be used. Of course, in practice, the status of an individual's haemoglobin profile is unknown at the time of measurement even if that sample is freshly drawn either from a finger stick injury or from venepuncture and, therefore, the assay's utility as a point of care method is compromised, as unacceptable inaccuracies could occur.

Moreover, clinical assays for HbA1c and other glycated haemoglobins are often subjected to a process of verification involving the distribution of stored blood samples by a central laboratory and their simultaneous analysis by different systems. If the assay does not perform identically between fresh patient samples and stored or laboratory manipulated blood samples, unacceptable bias will occur and the assay will fail to achieve the correct values.

Therefore, in addition to the simplification of the instrumentation and measurement requirements, an additional benefit of the present invention is the fact that an optical density measurement based on the intrinsic fluorescence quenching of the sample (FOD) reduces errors that may be introduced into the test methodology by variations in the composite spectrum of a given individual's haemoglobin profile because the spectra of the various haemoglobin types at these wavelengths are more closely matched.

Figure 5:
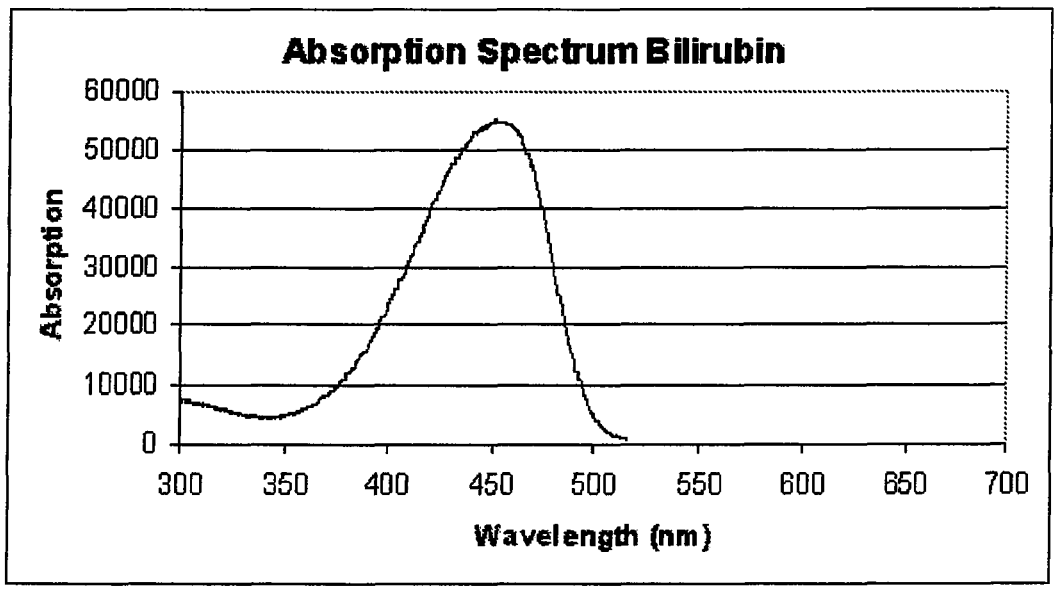
FIG. 5 is a graph showing the absorption spectrum of bilirubin.

A final benefit from the present invention is the reduction of errors caused by the presence of many interfering factors that might influence absorption measurements at 405 or 415 nm. For example, patients who suffer from liver disease that manifests itself in jaundice (i.e. yellowing of the skin and eyeballs) have high circulating levels of bilirubin. Bilirubin is a circulating by-product of haemoglobin metabolism and has significant overlapping absorption with the major peaks of haemoglobin (FIG. 5). The method of the prior art, which estimated the background fluorescence quenching from an optical density measurement of haemoglobin at its major absorption peaks, would be influenced by elevated circulating levels of bilirubin. The present invention, by estimating total haemoglobin by background fluorescence quenching at wavelengths greater than 500 nm, eliminates this potential source of error.

EXAMPLE 1

A known volume (2.5 mL) of reagent comprising a buffer (principally HEPES) and a fluorescent market compound (Eosin Boronate) was introduced into a reaction cuvette. This was introduced into an apparatus according to the present invention and was exited at 510 nm. Blank fluorescence readings were taken at 1 second intervals.

Then a volume of blood, whose total haemoglobin content/ concentration and percentage of glycated haemoglobin is known, was introduced into the cuvette at time $t_0$ and mixed. The fluorescence at 510 nm was then measured every second up to 3 minutes reaction time. The time taken to effect mixing results in the fluorescence only being recorded from about the 7th second onwards.

The blank and blood readings of fluorescence signal and reference are laid out in Table 1 below.

TABLE 1

| Reading Number | Raw Fluorescence Data | | Fluorescence Signal Minus Fluorescence | Fluorescence Signal/ Fluorescence | |
|---|---|---|---|---|---|
| (Seconds) | Signal | Reference | Background | Reference | Fit |
| Blanks | | | | | |
| 1 | 3564362 | 51585883 | 3563988 | 0.069088436 | |
| 2 | 3564298 | 51585628 | 3563924 | 0.069087537 | |
| 3 | 3564874 | 51585846 | 3564500 | 0.069098411 | |
| 4 | 3566215 | 51586743 | 3565841 | 0.069123205 | |
| 5 | 3565496 | 51586091 | 3565122 | 0.069110141 | |
| Bloods | | | | | |
| 1 | 0 | 0 | −374 | | 0.0575 |
| 2 | 0 | 0 | −374 | | 0.0575 |
| 3 | 0 | 0 | −374 | | 0.0575 |
| 4 | 0 | 0 | −374 | | 0.0574 |
| 5 | 0 | 0 | −374 | | 0.0574 |
| 6 | 0 | 0 | −374 | | 0.0574 |
| 7 | 2955821 | 51583592 | 2955447 | 0.057294323 | 0.0573 |
| 8 | 2955062 | 51582679 | 2954688 | 0.057280623 | 0.0573 |
| 9 | 2953008 | 51583518 | 2952634 | 0.057239873 | 0.0573 |
| 10 | 2949933 | 51582543 | 2949559 | 0.057181341 | 0.0572 |
| 11 | 2949493 | 51583139 | 2949119 | 0.057172151 | 0.0572 |
| 12 | 2946591 | 51582599 | 2946217 | 0.05711649 | 0.0572 |
| 13 | 2945289 | 51583468 | 2944915 | 0.057090287 | 0.0571 |
| 14 | 2944638 | 51583291 | 2944264 | 0.057077863 | 0.0571 |
| 15 | 2943483 | 51583517 | 2943109 | 0.057055222 | 0.0571 |
| 16 | 2941483 | 51582296 | 2941109 | 0.057017799 | 0.0571 |
| 17 | 2939910 | 51584175 | 2939536 | 0.056985229 | 0.0570 |
| 18 | 2938487 | 51583010 | 2938113 | 0.056958929 | 0.0570 |
| 19 | 2937585 | 51582202 | 2937211 | 0.056942334 | 0.0570 |
| 20 | 2935457 | 51583227 | 2935083 | 0.056899949 | 0.0569 |
| 21 | 2934545 | 51584002 | 2934171 | 0.056881415 | 0.0569 |
| 22 | 2933246 | 51582555 | 2932872 | 0.056857827 | 0.0569 |
| 23 | 2932307 | 51583308 | 2931933 | 0.056838794 | 0.0569 |
| 24 | 2930244 | 51583334 | 2929870 | 0.056798771 | 0.0568 |
| 25 | 2928809 | 51583527 | 2928435 | 0.05677074 | 0.0568 |
| 26 | 2928925 | 51582154 | 2928551 | 0.0567745 | 0.0568 |
| 27 | 2927934 | 51582712 | 2927560 | 0.056754674 | 0.0568 |
| 28 | 2925072 | 51583693 | 2924698 | 0.056698112 | 0.0567 |
| 29 | 2924539 | 51582904 | 2924165 | 0.056688646 | 0.0567 |
| 30 | 2924052 | 51583196 | 2923678 | 0.056678884 | 0.0567 |
| 31 | 2921778 | 51582587 | 2921404 | 0.056635469 | 0.0567 |
| 32 | 2921581 | 51583313 | 2921207 | 0.056630853 | 0.0567 |
| 33 | 2918178 | 51581710 | 2917804 | 0.05656664 | 0.0566 |
| 34 | 2918348 | 51581902 | 2917974 | 0.056569725 | 0.0566 |
| 35 | 2916054 | 51582192 | 2915680 | 0.056524934 | 0.0566 |
| 36 | 2915194 | 51582289 | 2914820 | 0.056508155 | 0.0566 |
| 37 | 2914844 | 51582120 | 2914470 | 0.056501555 | 0.0565 |
| 38 | 2914629 | 51581901 | 2914255 | 0.056497627 | 0.0565 |
| 39 | 2912071 | 51581619 | 2911697 | 0.056448345 | 0.0565 |
| 40 | 2911685 | 51581776 | 2911311 | 0.056440689 | 0.0565 |
| 41 | 2909430 | 51580144 | 2909056 | 0.056398757 | 0.0565 |
| 42 | 2909121 | 51581358 | 2908747 | 0.056391439 | 0.0564 |
| 43 | 2908666 | 51581300 | 2908292 | 0.056382681 | 0.0564 |
| 44 | 2906914 | 51581161 | 2906540 | 0.056348867 | 0.0564 |
| 45 | 2905229 | 51581336 | 2904855 | 0.056316009 | 0.0564 |
| 46 | 2904469 | 51581125 | 2904095 | 0.056301506 | 0.0564 |
| 47 | 2903867 | 51580515 | 2903493 | 0.0562905 | 0.0564 |
| 48 | 2903108 | 51580361 | 2902734 | 0.056275954 | 0.0563 |
| 49 | 2902382 | 51580998 | 2902008 | 0.056261184 | 0.0563 |
| 50 | 2900836 | 51580764 | 2900462 | 0.056231466 | 0.0563 |
| 51 | 2899915 | 51580441 | 2899541 | 0.056213963 | 0.0563 |
| 52 | 2899699 | 51580109 | 2899325 | 0.056210137 | 0.0563 |
| 53 | 2899117 | 51579994 | 2898743 | 0.056198979 | 0.0563 |
| 54 | 2898402 | 51579715 | 2898028 | 0.056185421 | 0.0562 |
| 55 | 2896664 | 51580326 | 2896290 | 0.05615106 | 0.0562 |
| 56 | 2897052 | 51580613 | 2896678 | 0.05615827 | 0.0562 |
| 57 | 2896426 | 51580073 | 2896052 | 0.056146722 | 0.0562 |
| 58 | 2895070 | 51580024 | 2894696 | 0.056120486 | 0.0562 |
| 59 | 2894867 | 51579530 | 2894493 | 0.056117088 | 0.0562 |
| 60 | 2893832 | 51579129 | 2893458 | 0.056097458 | 0.0562 |

TABLE 1-continued

| Reading Number | Raw Fluorescence Data | | Fluorescence Signal Minus Fluorescence Background | Fluorescence Signal/ Fluorescence Reference | Fit |
|---|---|---|---|---|---|
| (Seconds) | Signal | Reference | | | |
| 61 | 2893835 | 51578832 | 2893461 | 0.056097839 | 0.0561 |
| 62 | 2893142 | 51580065 | 2892768 | 0.056083062 | 0.0561 |
| 63 | 2891979 | 51579300 | 2891605 | 0.056061346 | 0.0561 |
| 64 | 2891624 | 51580313 | 2891250 | 0.056053363 | 0.0561 |
| 65 | 2889838 | 51579562 | 2889464 | 0.056019553 | 0.0561 |
| 66 | 2890166 | 51579307 | 2889792 | 0.056026189 | 0.0561 |
| 67 | 2888871 | 51579263 | 2888497 | 0.05600113 | 0.0561 |
| 68 | 2888266 | 51579055 | 2887892 | 0.055989626 | 0.0560 |
| 69 | 2887788 | 51578116 | 2887414 | 0.055981378 | 0.0560 |
| 70 | 2887371 | 51578675 | 2886997 | 0.055972686 | 0.0560 |
| 71 | 2887694 | 51578175 | 2887320 | 0.055979491 | 0.0560 |
| 72 | 2887040 | 51578384 | 2886666 | 0.055966585 | 0.0560 |
| 73 | 2886642 | 51577925 | 2886268 | 0.055959366 | 0.0560 |
| 74 | 2885106 | 51577596 | 2884732 | 0.055929943 | 0.0560 |
| 75 | 2884262 | 51576184 | 2883888 | 0.05591511 | 0.0560 |
| 76 | 2884732 | 51577237 | 2884358 | 0.055923081 | 0.0560 |
| 77 | 2884096 | 51577591 | 2883722 | 0.055910366 | 0.0559 |
| 78 | 2883331 | 51576616 | 2882957 | 0.055896591 | 0.0559 |
| 79 | 2882382 | 51577518 | 2882008 | 0.055877214 | 0.0559 |
| 80 | 2883826 | 51577070 | 2883452 | 0.055905696 | 0.0559 |
| 81 | 2882045 | 51577415 | 2881671 | 0.055870792 | 0.0559 |
| 82 | 2881718 | 51577408 | 2881344 | 0.055864459 | 0.0559 |
| 83 | 2881424 | 51577078 | 2881050 | 0.055859116 | 0.0559 |
| 84 | 2881564 | 51576485 | 2881190 | 0.055862473 | 0.0559 |
| 85 | 2882487 | 51575751 | 2882113 | 0.055881164 | 0.0559 |
| 86 | 2879464 | 51575861 | 2879090 | 0.055822432 | 0.0559 |
| 87 | 2879806 | 51575495 | 2879432 | 0.055829459 | 0.0558 |
| 88 | 2878031 | 51575609 | 2877657 | 0.05579492 | 0.0558 |
| 89 | 2877710 | 51576230 | 2877336 | 0.055788025 | 0.0558 |
| 90 | 2876336 | 51576600 | 2875962 | 0.055760985 | 0.0558 |
| 91 | 2877713 | 51576006 | 2877339 | 0.055788325 | 0.0558 |
| 92 | 2877616 | 51576122 | 2877242 | 0.055786319 | 0.0558 |
| 93 | 2877104 | 51578012 | 2876730 | 0.055774348 | 0.0558 |
| 94 | 2874740 | 51577685 | 2874366 | 0.055728868 | 0.0558 |
| 95 | 2875728 | 51576443 | 2875354 | 0.055749366 | 0.0558 |
| 96 | 2874720 | 51576213 | 2874346 | 0.055730071 | 0.0558 |
| 97 | 2875418 | 51576641 | 2875044 | 0.055743142 | 0.0558 |
| 98 | 2875735 | 51576325 | 2875361 | 0.055749629 | 0.0558 |
| 99 | 2875128 | 51576472 | 2874754 | 0.055737701 | 0.0557 |
| 100 | 2874927 | 51576492 | 2874553 | 0.055733783 | 0.0557 |
| 101 | 2874846 | 51576435 | 2874472 | 0.055732274 | 0.0557 |
| 102 | 2873640 | 51576098 | 2873266 | 0.055709255 | 0.0557 |
| 103 | 2873382 | 51575645 | 2873008 | 0.055704742 | 0.0557 |
| 104 | 2872954 | 51576065 | 2872580 | 0.05569599 | 0.0557 |
| 105 | 2872727 | 51575160 | 2872353 | 0.055692566 | 0.0557 |
| 106 | 2871226 | 51575773 | 2870852 | 0.055662801 | 0.0557 |
| 107 | 2872402 | 51575375 | 2872028 | 0.055686032 | 0.0557 |
| 108 | 2872774 | 51576582 | 2872400 | 0.055691942 | 0.0557 |
| 109 | 2870911 | 51575349 | 2870537 | 0.055657151 | 0.0557 |
| 110 | 2871892 | 51575295 | 2871518 | 0.05567623 | 0.0557 |
| 111 | 2870390 | 51575094 | 2870016 | 0.055647325 | 0.0557 |
| 112 | 2870840 | 51576083 | 2870466 | 0.055654983 | 0.0557 |
| 113 | 2870388 | 51575798 | 2870014 | 0.055646526 | 0.0556 |
| 114 | 2869947 | 51574332 | 2869573 | 0.055639557 | 0.0556 |
| 115 | 2870353 | 51573855 | 2869979 | 0.055647944 | 0.0556 |
| 116 | 2869297 | 51574060 | 2868923 | 0.055627247 | 0.0556 |
| 117 | 2868911 | 51573600 | 2868537 | 0.055620259 | 0.0556 |
| 118 | 2868895 | 51573772 | 2868521 | 0.055619763 | 0.0556 |
| 119 | 2868030 | 51573821 | 2867656 | 0.055602939 | 0.0556 |
| 120 | 2868701 | 51574367 | 2868327 | 0.05561536 | 0.0556 |
| 121 | 2866233 | 51574457 | 2865859 | 0.05556741 | 0.0556 |
| 122 | 2867978 | 51573835 | 2867604 | 0.055601915 | 0.0556 |
| 123 | 2867313 | 51573376 | 2866939 | 0.055589516 | 0.0556 |
| 124 | 2867172 | 51573576 | 2866798 | 0.055586566 | 0.0556 |
| 125 | 2866858 | 51573178 | 2866484 | 0.055580907 | 0.0556 |
| 126 | 2867058 | 51573583 | 2866684 | 0.055584348 | 0.0556 |
| 127 | 2867722 | 51573210 | 2867348 | 0.055597625 | 0.0556 |
| 128 | 2867285 | 51574328 | 2866911 | 0.055587947 | 0.0556 |
| 129 | 2858225 | 51574505 | 2857851 | 0.055412088 | 0.0556 |
| 130 | 2867356 | 51573382 | 2866982 | 0.055590343 | 0.0556 |

TABLE 1-continued

| Reading Number | Raw Fluorescence Data | | Fluorescence Signal Minus Fluorescence Background | Fluorescence Signal/ Fluorescence Reference | Fit |
|---|---|---|---|---|---|
| (Seconds) | Signal | Reference | | | |
| 131 | 2863993 | 51573955 | 2863619 | 0.055524518 | 0.0555 |
| 132 | 2865453 | 51573157 | 2865079 | 0.055553687 | 0.0555 |
| 133 | 2865181 | 51574269 | 2864807 | 0.055547215 | 0.0555 |
| 134 | 2864123 | 51573728 | 2863749 | 0.055527283 | 0.0555 |
| 135 | 2864932 | 51572876 | 2864558 | 0.055543887 | 0.0555 |
| 136 | 2863379 | 51572485 | 2863005 | 0.055514195 | 0.0555 |
| 137 | 2863690 | 51573048 | 2863316 | 0.055519619 | 0.0555 |
| 138 | 2864278 | 51572945 | 2863904 | 0.055531132 | 0.0555 |
| 139 | 2864629 | 51572443 | 2864255 | 0.055538478 | 0.0555 |
| 140 | 2862974 | 51573092 | 2862600 | 0.055505689 | 0.0555 |
| 141 | 2863867 | 51572498 | 2863493 | 0.055523644 | 0.0555 |
| 142 | 2863679 | 51573115 | 2863305 | 0.055519334 | 0.0555 |
| 143 | 2862000 | 51572406 | 2861626 | 0.055487541 | 0.0555 |
| 144 | 2862424 | 51573097 | 2862050 | 0.055495019 | 0.0555 |
| 145 | 2861464 | 51572506 | 2861090 | 0.05547704 | 0.0555 |
| 146 | 2862311 | 51572555 | 2861937 | 0.055493411 | 0.0555 |
| 147 | 2862304 | 51571108 | 2861930 | 0.055494832 | 0.0555 |
| 148 | 2862010 | 51571937 | 2861636 | 0.05548824 | 0.0555 |
| 149 | 2859734 | 51572024 | 2859360 | 0.055444014 | 0.0555 |
| 150 | 2860693 | 51571533 | 2860319 | 0.055463137 | 0.0555 |
| 151 | 2860913 | 51571985 | 2860539 | 0.055466917 | 0.0555 |
| 152 | 2862295 | 51572314 | 2861921 | 0.05549336 | 0.0555 |
| 153 | 2861267 | 51571491 | 2860893 | 0.055474312 | 0.0555 |
| 154 | 2861138 | 51572499 | 2860764 | 0.055470727 | 0.0555 |
| 155 | 2860113 | 51570936 | 2859739 | 0.055452532 | 0.0555 |
| 156 | 2859600 | 51571386 | 2859226 | 0.055442101 | 0.0555 |
| 157 | 2860578 | 51571930 | 2860204 | 0.05546048 | 0.0555 |
| 158 | 2858371 | 51571186 | 2857997 | 0.055418485 | 0.0554 |
| 159 | 2859688 | 51570801 | 2859314 | 0.055444436 | 0.0554 |
| 160 | 2860773 | 51571318 | 2860399 | 0.055464919 | 0.0554 |
| 161 | 2857694 | 51570305 | 2857320 | 0.055406304 | 0.0554 |
| 162 | 2859769 | 51570656 | 2859395 | 0.055446163 | 0.0554 |
| 163 | 2859690 | 51571693 | 2859316 | 0.055443516 | 0.0554 |
| 164 | 2859449 | 51570510 | 2859075 | 0.055440115 | 0.0554 |
| 165 | 2860192 | 51570519 | 2859818 | 0.055454513 | 0.0554 |
| 166 | 2858530 | 51569196 | 2858156 | 0.055423707 | 0.0554 |
| 167 | 2858942 | 51570525 | 2858568 | 0.055430268 | 0.0554 |
| 168 | 2858447 | 51570477 | 2858073 | 0.055420721 | 0.0554 |
| 169 | 2857559 | 51570836 | 2857185 | 0.055403116 | 0.0554 |
| 170 | 2857736 | 51570526 | 2857362 | 0.055406881 | 0.0554 |
| 171 | 2857315 | 51569676 | 2856941 | 0.055399631 | 0.0554 |
| 172 | 2857600 | 51569981 | 2857226 | 0.055404829 | 0.0554 |
| 173 | 2858461 | 51570608 | 2858087 | 0.055420851 | 0.0554 |
| 174 | 2856840 | 51570008 | 2856466 | 0.055390063 | 0.0554 |
| 175 | 2857004 | 51569874 | 2856630 | 0.055393387 | 0.0554 |
| 176 | 2856544 | 51569621 | 2856170 | 0.055384739 | 0.0554 |
| 177 | 2856786 | 51569880 | 2856412 | 0.055389154 | 0.0554 |
| 178 | 2856348 | 51570223 | 2855974 | 0.055380292 | 0.0554 |
| 179 | 2857336 | 51569511 | 2856962 | 0.055400215 | 0.0554 |
| 180 | 2857080 | 51570092 | 2856706 | 0.055394627 | 0.0554 |

In addition to the raw fluorescence data, Table 1 also shows various mathematical operations carried out on that data. The first mathematical operation is to subtract this fluorescence background ($F_{Bgd}$) from the raw fluorescence data, for both blank and the blood readings. The fluorescence background signal ($F_{Bgd}$) is derived from a reading of the buffer solution, with no fluorescent marker reagent present and has previously been measured. It is predominantly a reader constant, this background is principally the electrical zero of the fluorimeter; as the fluorimeter optical filters have been optimised to reduce 'filter breakthrough' from the buffer effectively to 'zero'.

The last three of the blank readings are averaged in order to establish $F_{Blank}$.

Figure 6:
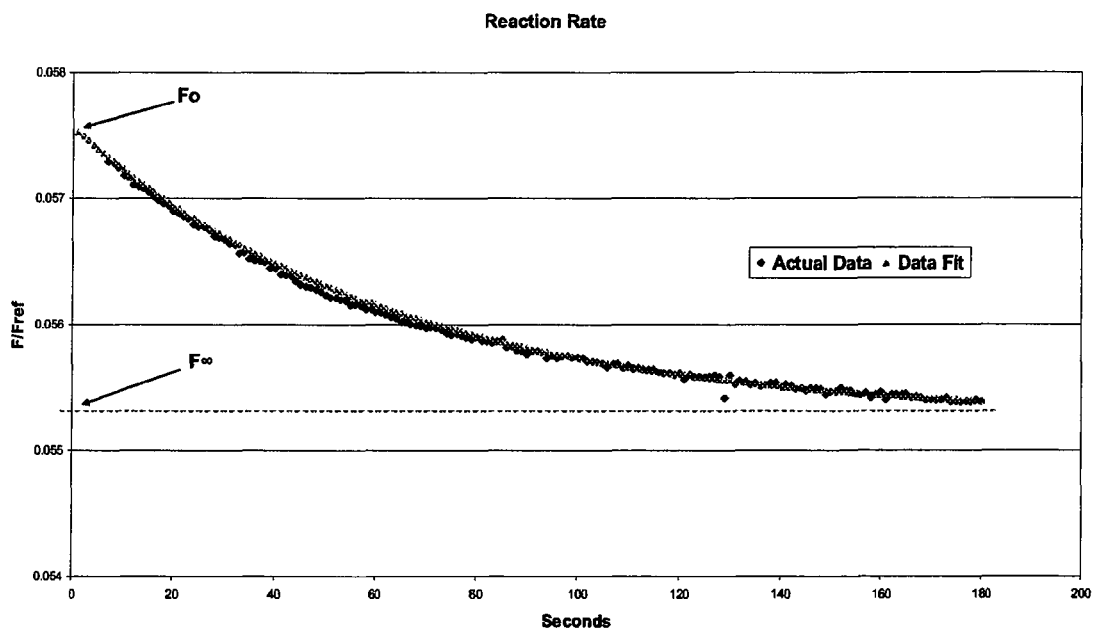
FIG. 6 is a graph plot of fluorescence data against time for sample 1 in Example 1.

The corrected fluorescence data is then divided by the reference. If this is plotted against time it produces a curve as shown in FIG. 6. A curve is fitted to these values using a suitable algorithm as previously discussed and the values (as shown the right hand column) are also plotted on the graph in FIG. 6. The values $F_0$ and $F_\infty$ can be derived for this sample by back and forward extrapolation of the data fit to $t_0$ and $t_\infty$ respectively.

Table 2 shows the results of an equivalent assay run on 20 samples. The sample (sample 1) assay shown in Table 1 is accompanied by 19 others who also had known reference amounts of total Haemoglobin (Total Hb), the concentration of glycated haemoglobin ([A1c]) and percentage glycated haemoglobin (% A1c).

$F_{blank}$ (corrected) is the average of the "Fluorescence Signal/Fluorescence Reference" values for the blanks in Table 1.

For each sample, the Fluorescence Optical Density (FOD) and Specific Quenching (SQ) are calculated from $F_{Blank}$, $F_0$ and $F_\infty$ using the formulae below;

$$FOD = \text{Log} \left[ (F_{Blank} - F_{Bgd})/(F0 - F_{Bgd}) \right] \quad \text{[Equation 1B]}$$

$$SQ = (F_0 - F_\infty)/(F_0 - F_{Bgd}) \quad \text{[Equation 3]}$$

From FOD and SQ the concentrations of total haemoglobin and glycated haemoglobin (A1c) concentrations are calculated by respectively.

$$[Total\ Hb] = m \cdot FOD + c \qquad \text{[Equation 4]}$$

$$[A1c] = m' \cdot SQ + c' \qquad \text{[Equation 5]}$$

The calibration constants m, m', c & c' are derived from standard curve (straight line) assay data using samples of known [A1c] and [Total Hb] concentrations. For the sample data provided c & c' are zero as the data has been constrained in both plots to go through zero.

The percentage glycated haemoglobin in the sample is then calculated thus;

$$\%A1c = ([A1c]/[Hb]) \cdot 100\% \qquad \text{[Equation 6]}$$

$$\%A1c = ((m' \cdot SQ + c')/(m \cdot FOD + c)) \cdot 100 \qquad \text{[Equation 7]}$$

Figure 8:
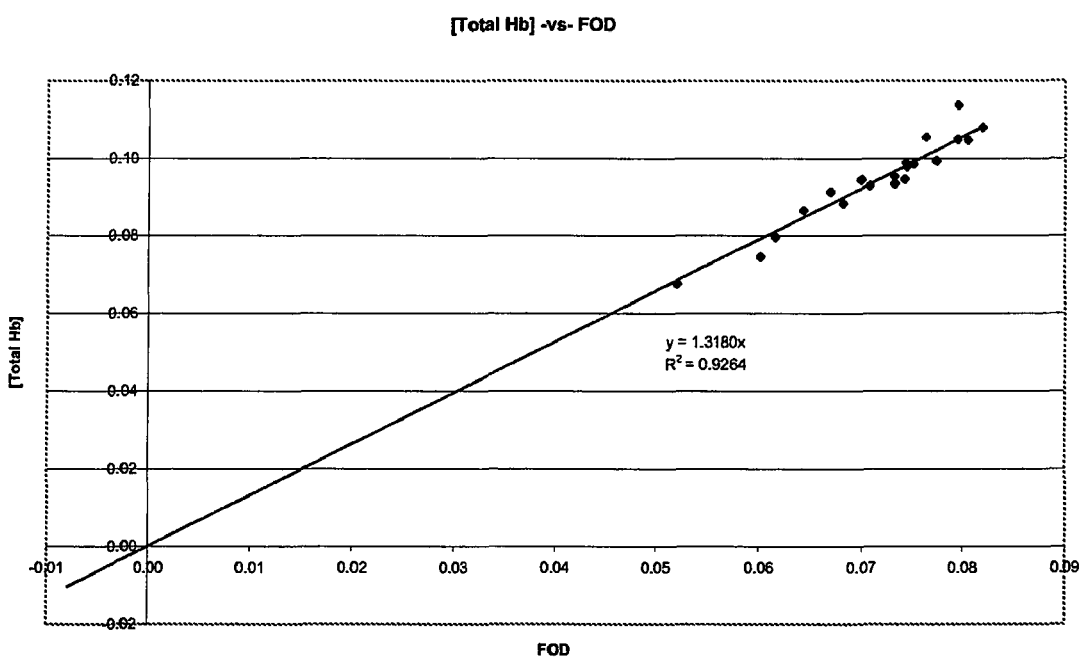
FIG. 8 is a plot of total haemoglobin concentration v Fluorescence Optical Density (FOD) for Example 1.

If the value of the Total Haemoglobin concentration is plotted against FOD they have been found to be directly proportional and the graph may be summarised according to the equation y=mx+c in which y is the total Haemoglobin concentration and x is FOD. m and c can then be calculated for a particular set of specific reaction parameters to give a standard calibration curve. FIG. 8 shows [Total Hb] v FOD for samples 1 to 20 with the line fitted thereto being summarised by the equation y=mx+c.

Figure 7:
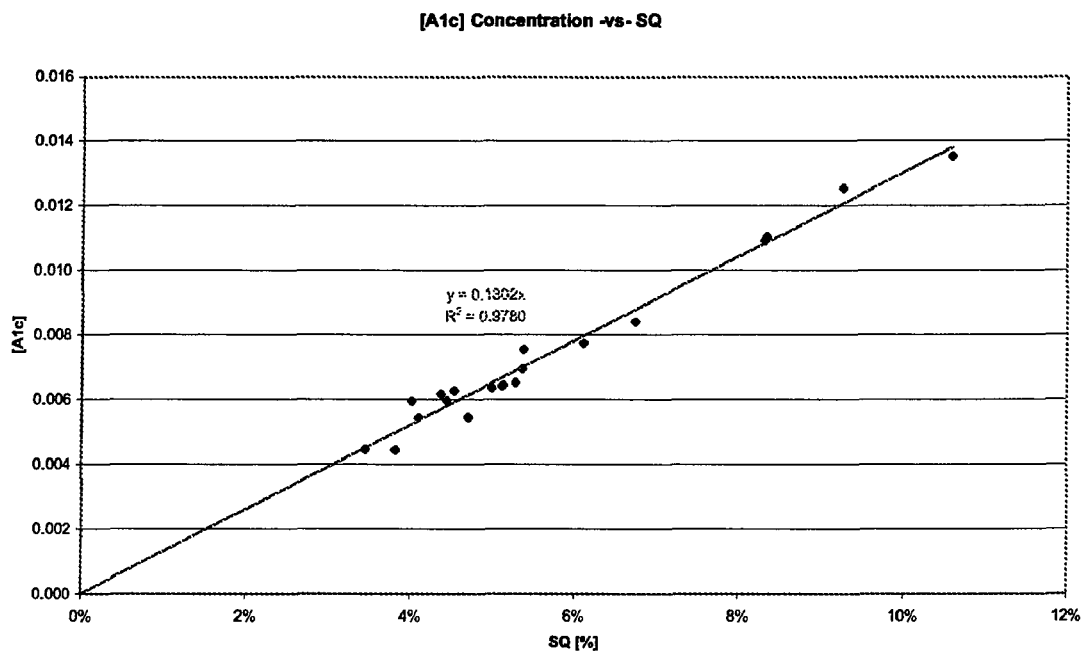
FIG. 7 is a plot of Glycated haemoglobin concentration v Specific Quenching for Example 1.

Likewise Specific quenching (SQ) has been found to directly proportional to the concentration of A1c, and the graph may be summarised according to the equation y=m'x+c' in which y is the glycated Haemoglobin concentration and x is specific quenching. m' and c' can then be calculated for a particular set of specific reaction conditions to give further standards. FIG. 7 shows [A1c] v SQ for samples 1 to 20 with the line fitted thereto being summarised by the equation y=m'x+c'.

For this example the standards derived from these are shown below in table 3.

TABLE 3

| | |
|---|---|
| [A1c] – vs. – SQ Slope = m' | 0.1302 |
| [A1c] – vs. – SQ Intercept = c' | 0 |
| [Total Hb] – vs. – FOD Slope = m | 1.318 |
| [Total Hb] – vs. – FOD Intercept = c | 0 |

These calibration constants are derived for a particular set of reaction criteria, and these may be used for subsequent assays using the same criteria. Different reaction conditions may require different calibration constants to be derived.

Table 2 shows the calculated values of % Glycated Haemoglobin and a comparison to the known value indicates the accurate nature of the assay of the present invention. Indeed the standard deviation of the error in the sample data set is just 0.4% A1c, demonstrating the accuracy of the present invention.

TABLE 2

| Sample Number | Reference %A1c | Reference [A1c] | Reference [Total Hb] | $F_{blank}$ (corrected) | Derived $F_o$ | Derived $F_\infty$ | Inherent Fluorescence Quenching | Specific Fluorescence Quenching | FOD | Measured %A1c |
|---|---|---|---|---|---|---|---|---|---|---|
| 1 | 5.65% | 0.0059 | 0.1052 | 0.06863 | 0.05757 | 0.05525 | 16.12% | 4.01% | 0.07636 | 5.19% |
| 2 | 5.05% | 0.0045 | 0.0881 | 0.06487 | 0.05545 | 0.05354 | 14.52% | 3.44% | 0.06812 | 5.00% |
| 3 | 11.05% | 0.0125 | 0.1135 | 0.07210 | 0.06003 | 0.05448 | 16.74% | 9.25% | 0.07955 | 11.49% |
| 4 | 10.25% | 0.0110 | 0.1077 | 0.06689 | 0.05540 | 0.05078 | 17.18% | 8.33% | 0.08188 | 10.05% |
| 5 | 5.95% | 0.0054 | 0.0913 | 0.06983 | 0.05987 | 0.05741 | 14.26% | 4.10% | 0.06683 | 6.06% |
| 6 | 6.35% | 0.0063 | 0.0987 | 0.06716 | 0.05661 | 0.05404 | 15.72% | 4.54% | 0.07426 | 6.03% |
| 7 | 8.95% | 0.0077 | 0.0864 | 0.06802 | 0.05867 | 0.05509 | 13.75% | 6.11% | 0.06426 | 9.39% |
| 8 | 8.75% | 0.0065 | 0.0744 | 0.06656 | 0.05796 | 0.05490 | 12.92% | 5.28% | 0.06009 | 8.67% |
| 9 | 6.85% | 0.0064 | 0.0928 | 0.06544 | 0.05560 | 0.05283 | 15.03% | 4.99% | 0.07075 | 6.96% |
| 10 | 6.55% | 0.0044 | 0.0675 | 0.07662 | 0.06797 | 0.06537 | 11.30% | 3.81% | 0.05205 | 7.24% |
| 11 | 6.75% | 0.0064 | 0.0952 | 0.06598 | 0.05575 | 0.05289 | 15.51% | 5.13% | 0.07318 | 6.93% |
| 12 | 11.55% | 0.0109 | 0.0944 | 0.08622 | 0.07268 | 0.06664 | 15.70% | 8.31% | 0.07415 | 11.07% |
| 13 | 7.60% | 0.0075 | 0.0993 | 0.06407 | 0.05362 | 0.05074 | 16.31% | 5.38% | 0.07734 | 6.87% |
| 14 | 6.80% | 0.0064 | 0.0944 | 0.06394 | 0.05443 | 0.05165 | 14.87% | 5.11% | 0.06993 | 7.22% |
| 15 | 7.05% | 0.0069 | 0.0983 | 0.06689 | 0.05628 | 0.05326 | 15.87% | 5.36% | 0.07503 | 7.06% |
| 16 | 6.85% | 0.0054 | 0.0795 | 0.06779 | 0.05883 | 0.05606 | 13.22% | 4.70% | 0.06158 | 7.54% |
| 17 | 12.95% | 0.0135 | 0.1045 | 0.07168 | 0.05956 | 0.05325 | 16.92% | 10.59% | 0.08048 | 13.00% |
| 18 | 6.10% | 0.0060 | 0.0977 | 0.06451 | 0.05436 | 0.05194 | 15.73% | 4.44% | 0.07435 | 5.90% |
| 19 | 5.90% | 0.0062 | 0.1046 | 0.06804 | 0.05667 | 0.05419 | 16.71% | 4.37% | 0.07942 | 5.44% |
| 20 | 9.00% | 0.0084 | 0.0934 | 0.06881 | 0.05813 | 0.05421 | 15.52% | 6.74% | 0.07324 | 9.09% |

The invention claimed is:

1. A method of carrying out an assay for a non-fluorescent substance in an assay sample, which method comprises:
   (a) carrying out a binding reaction in solution between a non-fluorescent substance in an assay sample and a fluorescent marker compound, the sample and marker compound being combined at time $t_0$;
   (b) exciting the fluorescence in the marker compound, wherein the nature of the marker and the nature of the excitation are such that the said fluorescence occurs at a wavelength at which said fluorescence is altered by the binding reaction of the marker compound with the non-fluorescent substance;
   (c) detecting, at multiple time points, resulting fluorescence data as the reaction progresses;
   (d) calculating from the detected fluorescence data the values of $F_0$ being the fluorescence at time $t_0$ and $F_\infty$ being the fluorescence at time $t_\infty$, when all of the non-fluorescent substance has reacted with the marker compound;
   (e) calculating from the values of $F_0$ and $F_\infty$ the change in fluorescence attributable to the reaction in step (a); and
   (f) determining from the calculated values and a calibration algorithm the concentration of the non-fluorescent substance present in the sample at $t_0$ prior to reacting with the fluorescent marker compound.

2. A method as claimed in claim 1, in which prior to step (a) the marker compound is excited and the resultant initial fluorescence ($F_{Blank}$) is detected.

3. A method as claimed in claim 2, in which the values of $F_0$ and $F_{Blank}$ are used to calculate the fluorescence optical density (FOD) using the equation:

$$FOD = \text{Log}\,[F_{Blank}/F_0] \qquad \text{(Equation 1)}.$$

4. A method as claimed in claim 2 where the non-fluorescent substance is a subspecies of a main substance, and the subspecies is selectively reactive with the marker compound, and wherein the overall concentration of the main substance and subspecies present in the sample at $t_0$, prior to reacting with the fluorescent marker compound, is determined from the calculated values of $F_0$, $F_\infty$ and $F_{Blank}$ and a suitable calibration algorithm of the form $y = m'x + c'$; where $m'$ and $c'$ are the slope and intercept calibration constants and $x = \text{Log}(F_{Blank}/F_0)$.

5. A method as claimed in claim 1 in which the calculation of the values of $F_0$ and $F_\infty$ in step (d) includes fitting a mathematical function of a curve of best fit to the fluorescence data detected in step (c) and extrapolating that function to time $t_0$ and $t_\infty$.

6. A method as claimed in claim 1 where the calibration algorithm used in step (f) is of the form $y = mx + c$, where m and c are the slope and intercept calibration constants and $x = (F_0 - F_\infty)/F_0$.

7. A method as claimed in claim 1, wherein the non-fluorescent substance to be assayed is a glycated protein.

8. A method as claimed in claim 7, wherein the marker compound contains a boronic acid group capable of selective binding with the cis-diol group of the glycated protein.

9. A method as claimed in claim 7, wherein the non-fluorescent substance is glycated haemoglobin.

10. A method as claimed in claim 1, wherein the fluorescent marker compound has a principal excitation wavelength in the range of 200nm to 800nm.

11. A method as claimed claim 1, wherein the fluorescent marker compound contains a fluorescein residue.

12. A method as claimed in claim 11, wherein the fluorescent compound is a group of the formula F—NH—CS—NH-Ph-B(OH)$_2$, wherein Ph is a phenyl group and F is a fluorescein residue.

13. A method as claimed in claim 11, wherein the fluorescent compound is a compound of the formula I:

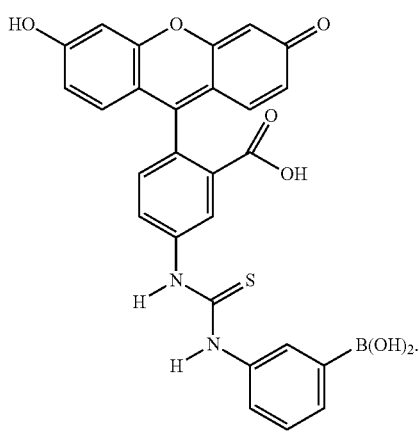

14. A method as claimed in claim 1, wherein the sample is selected from the group consisting of a blood sample, a plasma sample, a serum sample, and a urine sample.

15. A method as claimed in claim 14 wherein said sample comprises a blood sample.

16. A method of determining the concentration of a non-fluorescent substance, comprising exciting a fluorescent reagent, the excitation and emission spectrum of which overlaps the absorption spectrum of the non-fluorescent substance; detecting the resultant fluorescence; adding the non-fluorescent substance to the fluorescent reagent so that the substance reacts with the fluorescent reagent by binding thereto to alter the fluorescence over time; detecting a range of fluorescence values over a period of time starting at at least 5 seconds after the addition; using the range of measured fluorescence values to extrapolate a value for the fluorescence directl after addition of the substance at time $t_0$; and calculating the concentration of the non-fluorescent substance from the difference between the fluorescence detected before and after addition of the non-fluorescent substance.

17. Apparatus for the assay of a non-fluorescent substance, in a sample, which comprises:

(a) a supply of a fluorescent marker compound;

(b) a reaction vessel to hold an amount of the fluorescent marker compound and an assay sample containing a non-fluorescent substance, which together undergo a binding reaction beginning at time $t_0$ and ending at time $t_\infty$ that alters the fluorescent characteristics of the marker compound;

(c) a source of electro-magnetic radiation having a wavelength $\lambda_n$ to excite the fluorescence in the marker compound;

(d) detecting means to measure the resulting fluorescence at multiple time points as the reaction progresses; and (e) a processor to calculate from the measured fluorescence the values of $F_0$ being the fluorescence at time $t_0$, and $F_\infty$ being the fluorescence at time $t_\infty$ when all of the substance has reacted with the marker compound; to calculate any change in fluorescence not attributable to and that attributable to the reaction between the substance and the marker compound; and to determine from those calculated values the amount and/or concentration of the non-fluorescent substance and/or a sub-species thereof present in the sample at $t_0$.

18. Apparatus as claimed in claim 17, wherein the assay sample is a blood derived sample and the non-fluorescent substance in the assay sample is haemoglobin and/or glycated haemoglobin.

19. Apparatus as claimed in claim 17, in which $\lambda_n$ is approximately 510 nm.

* * * * *